United States Patent [19]

Lerner

[11] Patent Number: 4,838,787
[45] Date of Patent: Jun. 13, 1989

[54] ORTHODONTIC BRACKET AND LOCK PIN

[76] Inventor: Harry Lerner, Apartado Postal No. 64753, C.C.C.T., Caracas 1060-A, Venezuela

[21] Appl. No.: 96,865

[22] Filed: Sep. 15, 1987

[51] Int. Cl.$^4$ ............................................... A61C 7/00
[52] U.S. Cl. ...................................................... 433/14
[58] Field of Search ............................ 433/14, 8, 9, 11

[56] References Cited

U.S. PATENT DOCUMENTS

| | | |
|---|---|---|
| 1,821,171 | 9/1931 | Atkinson . |
| 2,019,773 | 11/1935 | Wirt . |
| 2,125,587 | 8/1938 | Richardson . |
| 2,196,516 | 4/1940 | Atkinson . |
| 2,305,916 | 12/1942 | Atkinson . |
| 2,686,365 | 8/1954 | Schurter . |
| 2,716,283 | 8/1955 | Atkinson . |
| 2,908,974 | 10/1959 | Stifter . |
| 2,971,258 | 2/1961 | Bien . |
| 3,119,182 | 1/1964 | Miller et al. . |
| 3,128,553 | 4/1964 | Begg . |
| 3,134,171 | 5/1964 | Kessler ................................. 433/14 |
| 3,163,933 | 1/1965 | Begg et al. ............................ 433/14 |
| 3,178,822 | 4/1965 | Fogel et al. . |
| 3,262,207 | 7/1966 | Kesling . |
| 3,335,496 | 8/1967 | Andrews et al. . |
| 3,574,940 | 4/1971 | Allesee . |
| 3,775,850 | 12/1973 | Northcutt . |
| 4,212,638 | 7/1980 | Korn . |
| 4,227,876 | 10/1980 | Fogel et al. . |
| 4,242,085 | 12/1980 | Wallshein . |
| 4,310,306 | 1/1982 | Wallshein . |
| 4,350,487 | 9/1982 | Kessling et al. ...................... 433/14 |
| 4,427,381 | 1/1984 | Hall . |
| 4,496,318 | 1/1985 | Connelly, Jr. . |

OTHER PUBLICATIONS

American Journal of Orthodontics, vol. 51 #10 "Improved Kessler Brackets".

Primary Examiner—Robert Peshock
Attorney, Agent, or Firm—Cushman, Darby & Cushman

[57] ABSTRACT

An orthodontic bracket device for use with the straight wire and light wire corrective techniques either singly or in combination. The bracket features intersecting securement slots for both reduced bulk and advantageous placement of the control wires closer to the tooth surface. In combination with a SHORT T-pin the two corrective techniques are simultaneously used without increasing the bulk of the bracket or wearer discomfort.

2 Claims, 4 Drawing Sheets

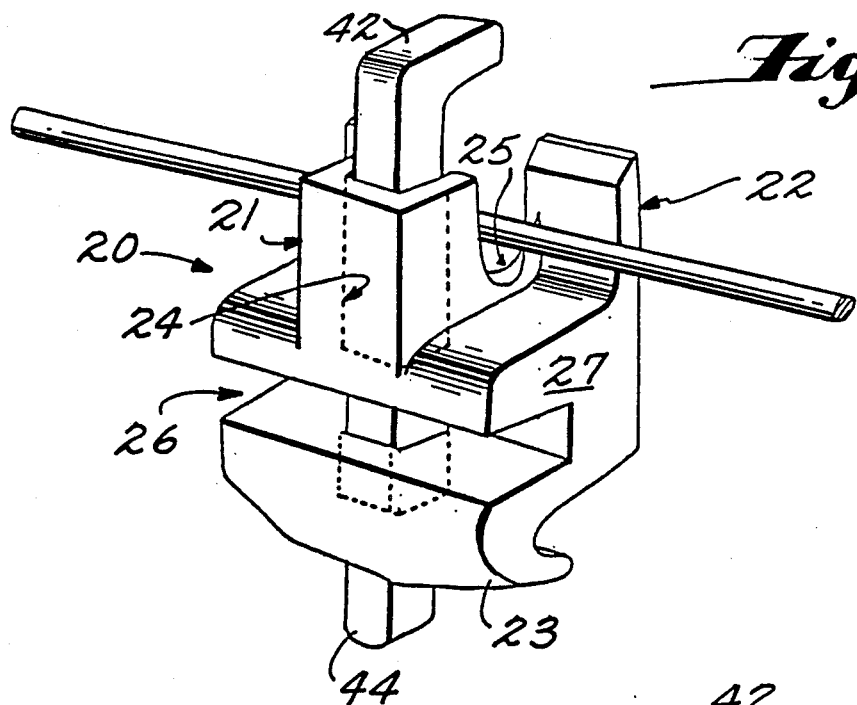
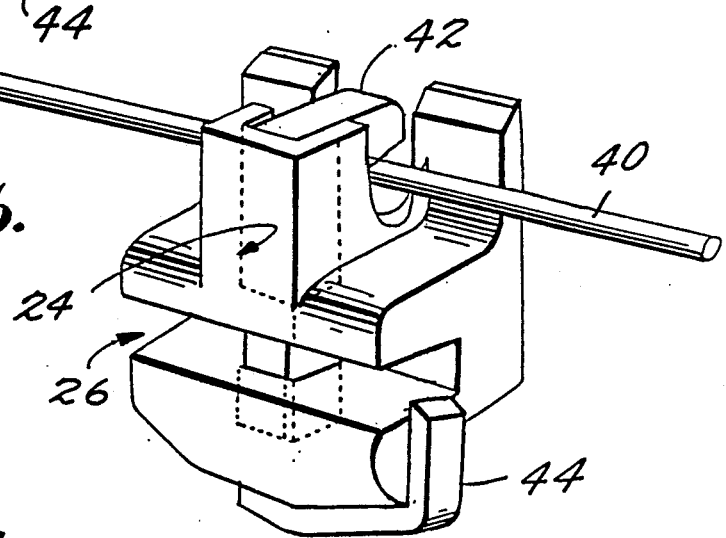
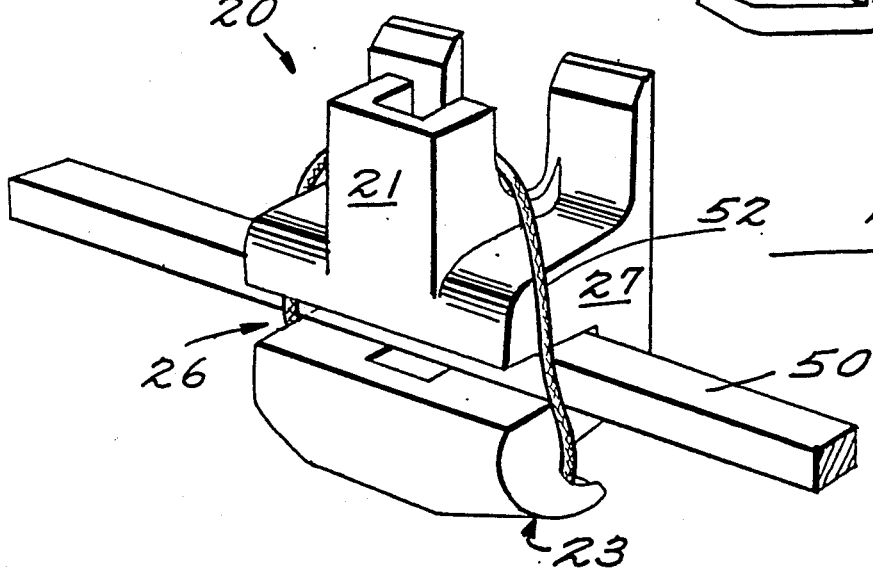

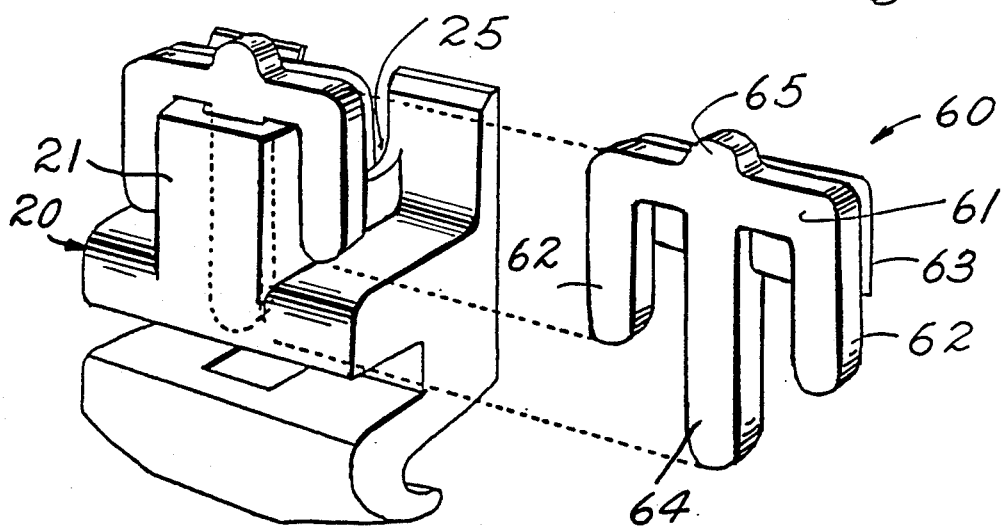
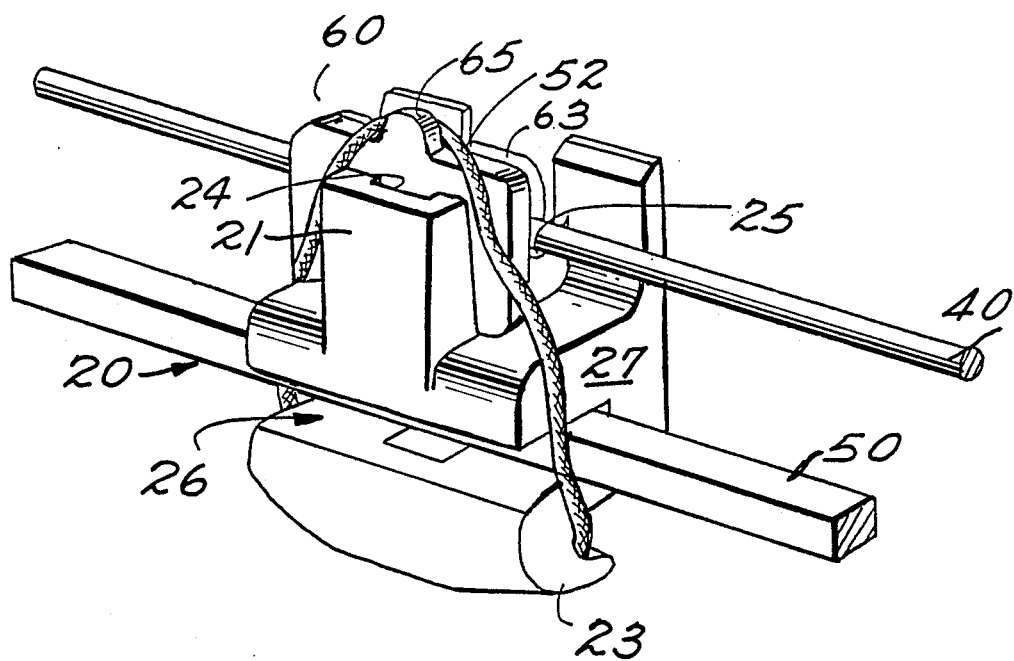

ORTHODONTIC BRACKET AND LOCK PIN

FIELD OF THE INVENTION

This invention relates to an orthodontic Bracket and associated Lock pin for use therewith. This bracket and lock pin advantageously allow the use of the commonly known Light wire and Edgewise orthodontic corrective techniques either singly or in combination.

BACKGROUND OF THE INVENTION

In conventional orthodontic treatments, two methods of treatment are primarily used. The first technique is known as the edgewise technique, which consists of applying moving force to the tooth by the use of a bracket having a rectangularly sectioned arch wire receiving slot with an arch wire received therein. The tooth is moved by the application of angular torque to the bracket by the square sectioned arch wire. This torque is transferred to the underlying tooth, attached to the bracket, which then moves in the desired direction. A variation on the edgewise technique is the Straight wire technique. In the straight wire technique, the torque and angulation are preadjusted in the bracket.

The second technique uses a lighter wire and is known as the Begg light wire technique. This technique is characterized by the application of a light, round sectioned arch wire, the force being applied to the tooth bracket by a different form of attachment of the light wire to the bracket. The result is similar to that of the rectangularly sectioned arch wire in that the energy stored in the wire by spring means is transferred to the tooth over time. It is very useful to have the versatility of a combination bracket that allows the use of either technique singly or both techniques simultaneously.

The problem associated with the prior art combination orthodontic brackets for use with the above discussed techniques is the bulkiness of the bracket. An example of a prior art tooth bracket is shown in FIGS. 1 and 2. The bracket 10 comprises a backing member 12 (for attachment to either a tooth band or the tooth directly), a body member 11 which has a horizontal slot 16 and vertical slot 14 located therein.

FIG. 2 illustrates the bracket of FIG. 1 using the light wire corrective technique. Conventional long pin 15 is inserted into the vertically oriented slot to wedge against and hold light wire 40 against the backing member of the bracket.

The bracket of FIGS. 1 and 2 is characterized by the location of the horizontal slot 16 in non-intersecting relation to vertical slot 14. This bracket configuration necessarily results in a relatively thicker, bulky, bracket which, because of its thickness, places the square arch wire a comparatively large distance from the surface of the tooth and impairs the performance thereof. Additionally, the increased bulk results in decreased wearer comfort due to the surrounding cheek tissue resiliently pressing against the protruding brackets and wires.

Examples of bulky prior art orthodontic bracket devices are disclosed in U.S. Pat. Nos. 4,496,318, 4,427,381, 4,227,876 and 3,163,933. Universally however, the prior art brackets are needlessly bulky and are, therefore, uncomfortable to the wearer and further provide inferior precision for the orthodontist.

SUMMARY OF THE INVENTION

A bracket according to the present invention combines the advantages of allowing single or simultaneous use of the straight wire and light wire corrective techniques with a low bulk bracket. Due to the intersecting configuration of the horizontal and vertical slots within the bracket, the bracket is necessarily characterized by reduced bulk and hence, increased comfort for the wearer and increased precision for the operator. An important element in the functionality of this bracket is the cooperating lock pin, which allows simultaneous use of the straight wire and light wire techniques. The lock pin of the present invention permits full, simultaneous, utilization of the horizontal and vertical slots without interference therebetween.

Other objects, features and characteristics of the present invention, as well as the methods and operation and functions of the related elements of the structure, and to the combination of parts and economies of manufacture, will become apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 6 is a bracket according to the present invention with a rectangular arch wire and elastic ligature in place.

FIG. 7 is a bracket and lock pin according to the present invention shown in perspective and removed views.

FIG. 8 is a bracket and lock pin according to the present invention with the rectangular and light wires in place.

DETAILED DESCRIPTION OF THE PREFERRED EMBODIMENT

Figure 3:
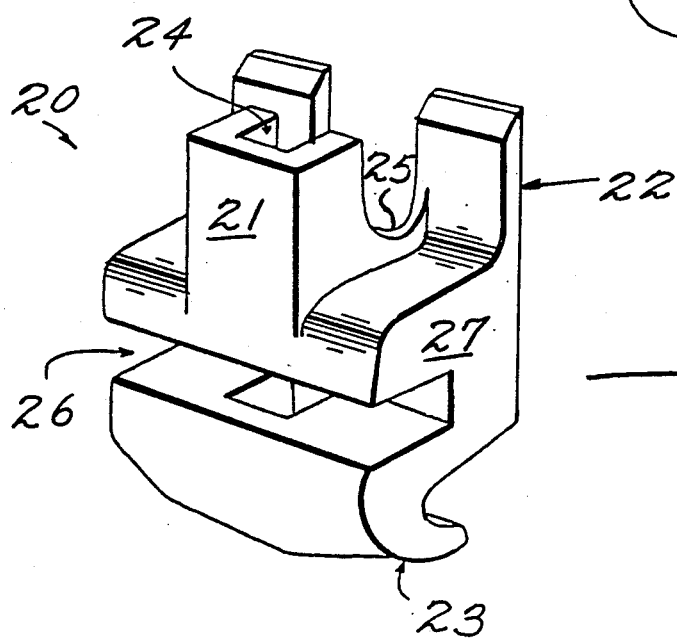
FIG. 3 is a perspective view of a bracket according to the present invention suitable for use with the edgewise corrective technique
Figure 3A:
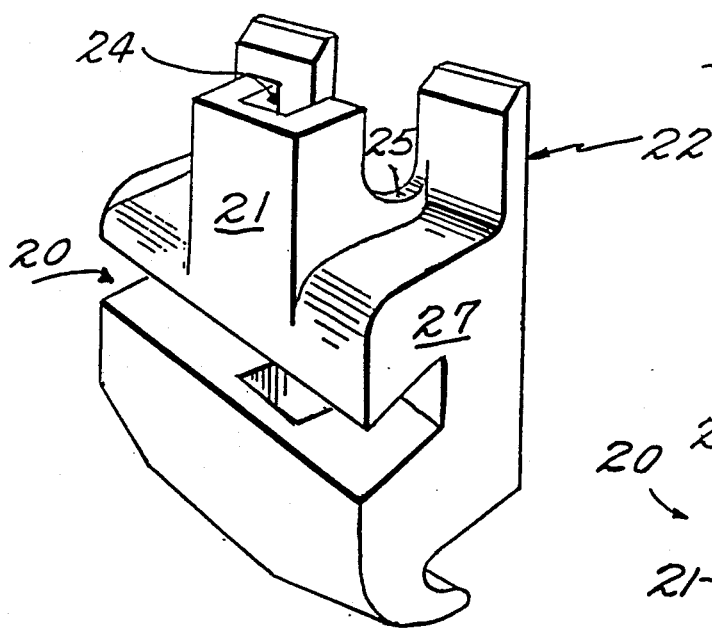
FIG. 3A is a perspective view of a bracket according to the present invention suitable for use with the straight wire corrective technique.

With reference to drawing FIGS. 3 and 3A the following description of a bracket according to the present invention is offered. Bracket 20 includes two major portions, a backing member 22 and a frontal body member connected thereto. The frontal body member comprises an upper frontal body member 21, center body member 27 and lower rearwardly curved body member 23. The backing member 22 functions so that the bracket 20 may be attached either to a band (around a tooth) or the tooth itself by an appropriate adhesive. The body members 21, 23 and 27 cooperate in a single contiguous body configuration and have the vertical and horizontal slots located therein.

The upper frontal body member 21 resembles a hollow rectangular block upended with a slot 24 running throughout the length thereof. The upper frontal body member 21 is positioned on top of center body member 27. Center body member 27 accommodates the substantially horizontal slot 26 and the extended portions of vertical slot 24. It should be noted that these slots 24 and 26 intersect in the region of the center body member 27. The rearwardly curved lower body member 23 forms the bottom of the frontal slot 26 and then curves downward and rearward from the bottom of the slot in order to function as a securement for an elastic ligature member (described in conjunction with FIG. 6).

FIG. 3 illustrates a bracket according to the present invention which is suited for use with the edgewise corrective technique wherein the torque and angulation forces are contained in the rectangular arch wire via the inherent resiliency of the wire. FIG. 3A illustrates a bracket according to the present invention for use with the straight wire technique wherein the torque and angulation forces are preadjusted (contained) in the bracket, i.e., the bracket contains angled slots to suit.

Between upper frontal body member 21 and the backing member 22, there exists a U-shaped wire guide 25. This wire guide 25 accommodates the light wire of the Begg corrective technique. The wire guide is also positioned rearward of the vertical slot 24 so that a locking pin may be inserted in the slot and wedge against a wire positioned in the wire guide 25.

Figure 4:
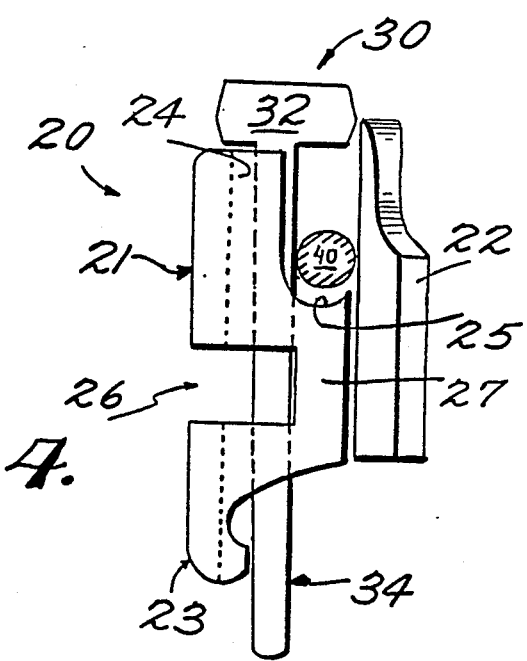
FIG. 4 is a lateral view of a bracket according to the present invention with locking pin and light wire in place.

The configuration shown in FIG. 4 demonstrates the use of a bracket according to the present invention using a single light wire technique.

Figure 1:
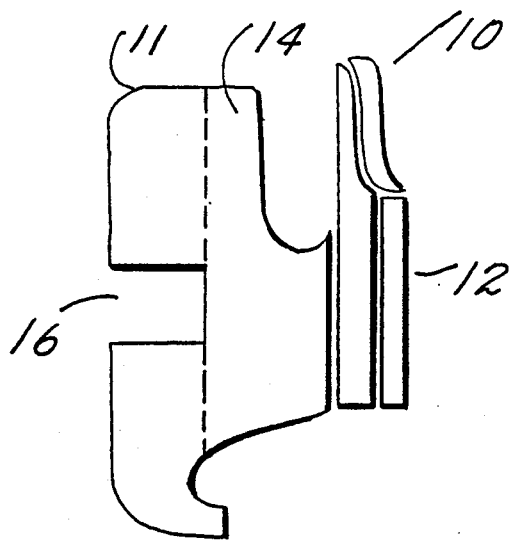
FIG. 1 is a lateral view of a prior art bracket device incorporating horizontal and vertical slots.
Figure 2:
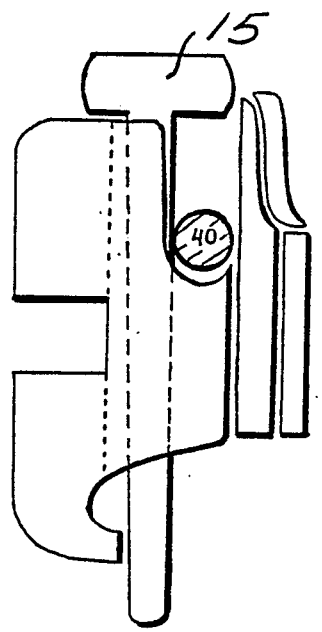
FIG. 2 is a lateral view of the bracket of FIG. 1 with a locking pin and light wire in place.

FIG. 4 illustrates bracket 20 with a light wire 40 and pin 30 in position. The pin 30 includes basically two members: a pin hat 32 and pin stay shaft member 34. These elements of the pin 30 cooperate to engage vertical slot 24, the rearward edge of the rearwardly curved lower body portion 23, and the backing member 22 in order to wedge and securely retain wire member 40. At this point it is important to notice that body portions 21 and 23 of bracket 20 are considerably thinner as compared to body portion 11 of the prior art bracket of FIGS. 1 or 2. Thus, the vertical slot 24 intersects horizontal slot 26 and pin 30 obstructs horizontal slot 26.

Figure 5:
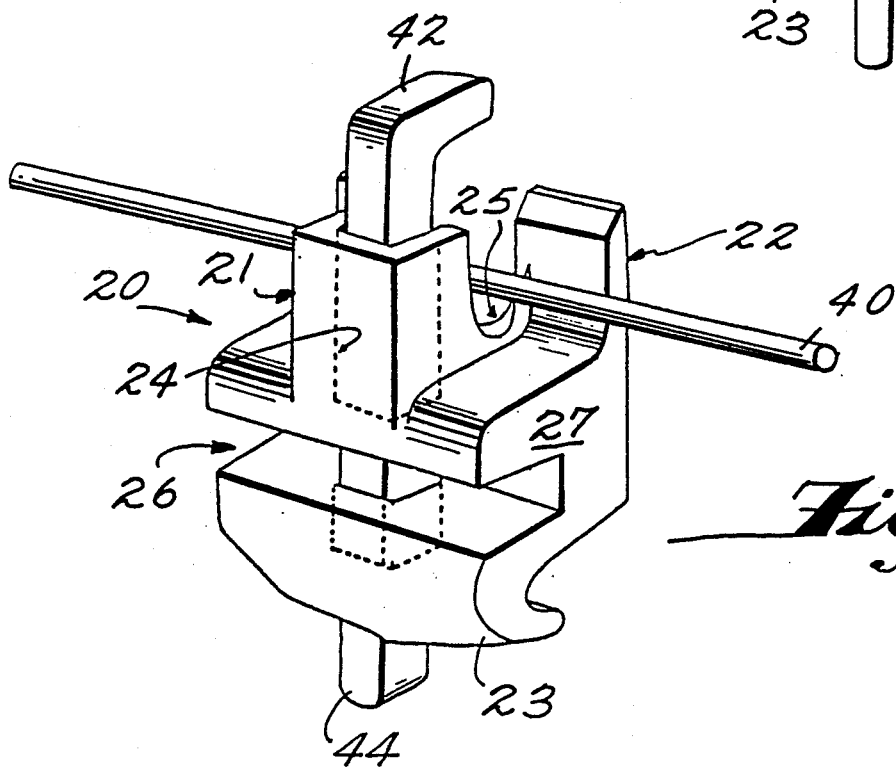
FIG. 5A is a perspective view of a bracket according to the present invention with locking pin and light wire in place.
FIG. 5B is the same view as in FIG. 5A only with the pin in a locked configuration.

FIG. 5A is a perspective view of the bracket and light wire member as shown in FIG. 4, but with a different kind of locking pin 42. The configuration, however, is identical to that of FIG. 4 and all of the like elements function in a similar manner. The locking pin 42 may be of any convenient configuration as long as the basic locking function against light wire 40 is accomplished.

It is important to point out that the long length of the pins, enables them to extend through the vertical slot of the bracket and be secured in place by bending, around the bottom of the bracket, an end of the shank which extends from the end of the lock pin channel remote from the lock pin head. (FIG. 5A shows the pin "unlocked" and FIG. 5B shows the pin "locked")

FIG. 6 shows a perspective view of bracket 20 when the edgewise or straight wire technique is used alone with a rectangular arch wire 50 inserted and held in frontal slot 26. The arch wire is held in place by an elastic ligature member 52. The elastic ligature member hooks over the top portion of the upper frontal body portion 21 of bracket 20. The ligature member then extends over the arch wire 50 along the side of the bracket and loops around below the arch wire and hooks onto the rearwardly curved lower body portion 23 of bracket 20. Thus, the rectangular arch wire 50 is securely fastened within frontal slot 26 and is able to impart any required forces to the underlying tooth. Due to the reduced bulk construction of the bracket 20, the arch wire 50 is positioned in close proximity to the surface of the tooth. Such positioning enables more precise control over tooth movement than with the prior art bracket illustrated in FIG. 1.

FIG. 7 is a perspective view of bracket 20 and the short T-pin 60 of the present invention. This unique pin greatly assists in the simultaneous use of the edgewise and light wire corrective techniques. The pin consists of a stay shaft 64, lateral wings 62, and a top T-portion 61. The stay shaft 64 is short, just the length of the upper frontal body member 21, so when it's inserted into the vertical slot 24 of bracket 20 it does not pass through the horizontal slot while the lateral wings simultaneously slipover the side portions of the upper frontal body portion 21 and provides stability to the pin and avoids any movement thereof. This T-formation enables the lateral wings 62 to engage the side surfaces of the upper body portion 21. Additionally, the SHORT T-pin 60 has a backing wedge member 63. The backing wedge functions so as to securely hold a light wire received in the U-shaped wire guide 25. An additional feature of this SHORT T-pin is extension 65. When the T-pin is inserted into bracket 20, it is seen that the lateral wings extend beside body portion 21 and obstruct the previous wrapping path of the ligature (as shown in FIG. 6). The extension 65 enables the wrapping of the ligature member over the top of the pin to further secure the pin in position. Extension 65 allows a ligature member to merely hook behind the extension rather than completely wrap the lateral wings of the T-pin and impair the performance of the pin by possibly encouraging its displacement upwards and out of the vertical slot. This configuration is shown in FIG. 8.

FIG. 8 illustrates bracket 20 when both the light wire and rectangular wire are being used simultaneously. A light wire 40 is inserted into wire guide 25; subsequently a rectangular arch wire 50 is inserted into frontal slot 26. The light wire 40 is held in place by the backing wedge 63 of SHORT T-pin 60. The SHORT T-pin is stabilized in position by the lateral wings being extended beside the upper frontal body portion. An elastic ligature member 52 is then extended over extension 65 to secure SHORT T-pin 60 and wraps in front of arch wire 50 and then below and around the rearwardly curved lower body portion 23 of bracket 20. In this configuration, both the rectangular and light wires are advantageously used with a bracket having substantially less bulk than prior art brackets. Further, the wires 40 and 50 maintain a close proximity to the underlying tooth and thus allow superior control and precision of tooth placement and movement. The combined result of the use of this bracket is comfort to the wearer and convenience to the operator.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An orthodontic bracket device for use with a light wire technique and edge wise correction technique, comprising:
   a backing plate for attachment to a tooth band or tooth; and,
   a body portion connected to said backing plate having a frontal slot located therein along a midsection thereof for receipt of an arch wire, said body portion also having a passageway located therethrough which intersects said frontal slot, said passageway extending upwardly through and upwardly protruding portion of said body portion, said upwardly protruding portion being positioned relative to said backing plate so as to create a light wire receiving channel therebetween, said body portion also having a lower portion located immediately beneath said frontal slot;
   said light wire receiving channel having a light wire received therein and said passageway having a locking pin means inserted therein for securing said light wire in said light wire receiving channel, said locking pin means having front and back sides and comprising a center shaft member connected on either side to a pair of lateral shaft members by a crossing T-member, the improvement comprising said center shaft extending through said crossing T-member to form an extension thereof, said lateral shaft members grippingly engaging the exterior side surfaces of said upwardly protruding portion, said center extending to, but not through, said frontal slot,
   said frontal slot having a rectangular arch wire received therein with portions thereof extending beyond said body portion of said bracket device, said arch wire being held securely in said frontal slot by elastic ligature means, said elastic ligature means looping around behind both said extension of said center shaft and said lower portion of said body portion and riding over said portions of said rectangular arch wire.

2. The invention as claimed in claim 1 wherein said locking pin means has a wedge member located on said back side thereof so as to coact with said light wire receiving channel to securely retain said light wire therein.

* * * * *